United States Patent
Garcia Molina et al.

(10) Patent No.: US 10,220,183 B2
(45) Date of Patent: Mar. 5, 2019

(54) ADJUSTMENT OF SENSORY STIMULATION INTENSITY TO ENHANCE SLEEP SLOW WAVE ACTIVITY

(71) Applicants: KONINKLIJKE PHILIPS N.V., Eindhoven (NL); WISCONSIN ALUMNI RESEARCH FOUNDATION, Madison, WI (US)

(72) Inventors: Gary Nelson Garcia Molina, Madison, WI (US); Michele Bellesi, Madison, WI (US); Brady Alexander Riedner, Middleton, WI (US); Giulio Tononi, Verona, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 623 days.

(21) Appl. No.: 14/784,746

(22) PCT Filed: Apr. 1, 2014

(86) PCT No.: PCT/IB2014/060344
§ 371 (c)(1),
(2) Date: Oct. 15, 2015

(87) PCT Pub. No.: WO2014/170781
PCT Pub. Date: Oct. 23, 2014

(65) Prior Publication Data
US 2016/0082222 A1    Mar. 24, 2016

Related U.S. Application Data

(60) Provisional application No. 61/812,908, filed on Apr. 17, 2013.

(51) Int. Cl.
*A61M 21/02* (2006.01)
*A61B 5/00* (2006.01)
(Continued)

(52) U.S. Cl.
CPC ........... *A61M 21/02* (2013.01); *A61B 5/0482* (2013.01); *A61B 5/4812* (2013.01);
(Continued)

(58) Field of Classification Search
CPC . A61B 5/4812; A61B 5/04845; A61B 5/0482; A61B 5/4815; A61B 5/6803; A61B 5/486; A61M 21/02
See application file for complete search history.

(56) References Cited

U.S. PATENT DOCUMENTS

2008/0081941 A1    4/2008   Tononi
2008/0234785 A1*   9/2008   Nakayama ........... A61B 5/0205
                                              607/62
(Continued)

FOREIGN PATENT DOCUMENTS

JP    2010035860 A    2/2010
JP    2011159108 A    8/2011
(Continued)

OTHER PUBLICATIONS

Landsness, Eric C., "Sleep-dependent improvement in visuomotor learning: a causal role for slow waves", Sleep vol. 32, issue 10, pp. 1273-84, Oct. 2009.
(Continued)

*Primary Examiner* — Kaylee R Wilson (57) ABSTRACT

A system is configured to provide sensory stimuli to a subject at a first intensity level, determine the effectiveness of the provided sensory stimuli, and incrementally increase the intensity level of the sensory stimuli based on the determined effectiveness. The effectiveness determination and the corresponding intensity increase are repeated one or more times during a given slow wave sleep episode. The system is configured to continue the effectiveness determinations and the corresponding intensity increases during the
(Continued)

slow wave sleep episode until the intensity level reaches a maximum level, until an arousal level of the subject breaches an arousal level threshold, and/or until expiration of the period of slow wave sleep.

21 Claims, 4 Drawing Sheets

(51) Int. Cl.
 *A61B 5/0482* (2006.01)
 *A61M 21/00* (2006.01)
(52) U.S. Cl.
 CPC ... *A61B 5/4815* (2013.01); *A61M 2021/0016* (2013.01); *A61M 2021/0022* (2013.01); *A61M 2021/0027* (2013.01); *A61M 2021/0044* (2013.01); *A61M 2021/0072* (2013.01); *A61M 2205/18* (2013.01); *A61M 2205/505* (2013.01); *A61M 2230/005* (2013.01); *A61M 2230/06* (2013.01); *A61M 2230/10* (2013.01); *A61M 2230/42* (2013.01); *A61M 2230/63* (2013.01)

(56) References Cited

U.S. PATENT DOCUMENTS

| | | | |
|---|---|---|---|
| 2009/0082639 A1 | 3/2009 | Pittman et al. | |
| 2012/0253221 A1 | 10/2012 | Hamaguchi et al. | |
| 2012/0311556 A1 | 12/2012 | Matsukawa | |
| 2013/0190556 A1* | 7/2013 | Wetmore | A61M 21/02 600/28 |

FOREIGN PATENT DOCUMENTS

| | | |
|---|---|---|
| RU | 2214931 C2 | 10/2003 |
| RU | 2304988 C2 | 8/2007 |
| UA | 50019 A | 10/2002 |

OTHER PUBLICATIONS

Landsness et al, "Sleep-Dependent Improvement in Visuomotor Learning: A Causal Role for SLWO Waves", Sleep, vol. 32, No. 10, 2009, pp. 1273-1284.

Colrain, "The K-Complex: A 7-Decade History", Sleep, vol. 28, No. 2, 2005, pp. 255-274.

Tononi, "Enhancing Sleep Slow Waves With Natural Stimuli", Medicamundi, vol. 54, No. 2, 2010, pp. 82-88.

Massimini, "Triggering Sleep Slow Waves by Transcranial Magnetic Stimulation", PNAS, vol. 104, No. 20, 2007, pp. 8496-8501.

Tononi et al, "Sleep Function and Synaptic Homeostasis", Sleep Medicine Reviews, vol. 10, 2006, pp. 49-62.

Dang-Vu, "Spontaneous Brain Rhythms Predict Sleep Stability in the Face of Noice", Current Biology, vol. 20, No. 15, pp. 1-12 (2010).

Hung et al, "Phase-Locked Loop Techniquest—A Survey", IEEE Transactions on Industrial Electronics, vol. 43, No. 6, 1996, pp. 609-615.

Tobler, "Phylogeny of Sleep Regulation", Principles and Practice of Sleep Medicine, 5th Edition, 2010, pp. 77-90.

Woods et al, "The Habituation of Event-Related Potentials to Speech Sounds and Tones", Electroencephalography and Clinical Neurophysiology, vol. 65, No. 6, 1986, pp. 447-459.

* cited by examiner

ADJUSTMENT OF SENSORY STIMULATION INTENSITY TO ENHANCE SLEEP SLOW WAVE ACTIVITY

CROSS-REFERENCE TO PRIOR APPLICATIONS

This application is the U.S. National Phase application under 35 U.S.C. § 371 of International Application Serial No. PCT/IB2014/060344, filed on Apr. 1, 2014, which claims the benefit of U.S. application Ser. No. 61/812,908, filed on Apr. 17, 2013. These applications are hereby incorporated by reference herein.

BACKGROUND

1. Field

The present disclosure pertains to a system and method for managing a current sleep session of a subject. One or more sensory stimulators incrementally increase the intensity of sensory stimuli provided to a subject during periods of slow wave sleep.

2. Description of the Related Art

Systems for monitoring sleep are known. Sensory stimulation during sleep is known. Sensory stimulation during sleep is often applied continuously at intervals and/or intensities that do not correspond to sleeping patterns of a subject. The present disclosure overcomes deficiencies in prior art systems.

SUMMARY

Accordingly, one or more aspects of the present disclosure relate to a system configured to manage a current sleep session of a subject. The system comprises one or more sensory stimulators, one or more sensors, and one or more processors. The one or more sensory stimulators are configured to provide sensory stimuli to the subject. The one or more sensors are configured to generate output signals conveying information related to a current sleep stage of the subject during the current sleep session. The one or more processors are configured to execute computer program modules. The computer program modules comprise a sleep stage module, a slow wave sleep timing module, a control module, an effectiveness module, and an adjustment module. The sleep stage module is configured to determine the current sleep stage of the subject based on the output signals. The sleep stage module is configured to determine whether the subject is presently in slow wave sleep. The slow wave sleep timing module is configured to determine individual time periods of slow wave sleep during the current sleep session based on the sleep stage determinations by the sleep stage module. The control module is configured to control the one or more sensory stimulators to provide the sensory stimuli to the subject during the individual time periods of slow wave sleep. The control module is configured to control the one or more sensory stimulators to provide the sensory stimuli at a first intensity level during a first individual time period of slow wave sleep. The effectiveness module is configured to determine an effectiveness of the provided sensory stimuli. The effectiveness is related to an increase in slow wave activity (SWA) caused by the sensory stimuli. In some embodiments, SWA corresponds to the power of an electroencephalogram signal in the 0.5-4.0 Hz band. In some embodiments, this band is set to 0.5-4.5 Hz. The effectiveness is determined based on the output signals. The effectiveness module is configured to determine a first effectiveness of the sensory stimuli provided at the first intensity level during the first individual time period. The adjustment module is configured to cause the one or more sensory stimulators to increase the intensity of the provided sensory stimuli based on the determined effectiveness. The intensity of the provided sensory stimuli is increased to a second intensity level based on the first effectiveness. The effectiveness module and the adjustment module are configured to repeat the effectiveness determination and the intensity increase one or more times during the individual time periods of slow wave sleep until expiration of the individual time periods such that the effectiveness module determines a second effectiveness of the sensory stimuli provided at the second intensity level during the first individual time period of slow wave sleep and the adjustment module causes the one or more sensory stimulators to increase the intensity of the provided sensory stimuli to a third intensity level. In some embodiments, the sleep stage module is configured to determine one or more arousal levels of the subject during the individual time periods of slow wave sleep. The adjustment module is configured to cause the sensory stimulators to decrease the intensity of, and/or cease providing, the sensory stimulation to the subject during a given period of slow wave sleep responsive to an arousal level determined by the sleep stage module breaching an arousal level threshold during the given period of slow wave sleep.

Yet another aspect of the present disclosure relates to a method for managing a current sleep session of a subject with a management system. The system comprises one or more sensory stimulators, one or more sensors, and one or more processors configured to execute computer program modules. The computer program modules comprise a sleep stage module, a slow wave sleep timing module, a control module, an effectiveness module, and an adjustment module. The method comprises generating, with the one or more sensors, output signals conveying information related to a current sleep stage of the subject during the current sleep session; determining, with the sleep stage module, the current sleep stage of the subject based on the output signals; determining, with the sleep stage module, whether the subject is presently in slow wave sleep based on the sleep stage determinations; determining, with the slow wave sleep timing module, individual time periods of slow wave sleep during the current sleep session based on the sleep stage determinations; controlling, with the control module, the one or more sensory stimulators to provide sensory stimuli to the subject during the individual time periods of slow wave sleep, the controlling including controlling the one or more sensory stimulators to provide the sensory stimuli at a first intensity level during a first individual time period of slow wave sleep; determining, with the effectiveness module, an effectiveness of the provided sensory stimuli, the effectiveness being related to an increase in slow wave activity caused by the sensory stimuli, the effectiveness being determined based on the output signals such that a first effectiveness of the sensory stimuli provided at the first intensity level during the first individual time period is determined; causing, with the adjustment module, the one or more sensory stimulators to increase the intensity of the provided sensory stimuli based on the determined effectiveness such that the intensity of the provided sensory stimuli is increased to a second intensity level based on the first effectiveness; and repeating, with the effectiveness module and the adjustment module, the effectiveness determination and the intensity increase one or more times during the individual time periods of slow wave sleep until expiration of the individual time periods such that a second effectiveness of the sensory stimuli provided at the second intensity level during the first individual time period of slow wave sleep is determined and the one or more sensory stimulators are caused to increase the intensity of the provided sensory stimuli to a third intensity level. In some embodiments, the method further comprises determining, with the sleep stage module, one or more arousal levels of the subject during the individual time periods of slow wave sleep, and causing, with the adjustment module, the sensory stimulators to decrease the intensity of and/or cease providing, the sensory stimulation to the subject during a given period of slow wave sleep responsive to an arousal level breaching an arousal level threshold during the given period of slow wave sleep.

Still another aspect of present disclosure relates to a system configured to manage a current sleep session of a subject. The system comprises means for providing sensory stimuli to the subject, means for generating output signals conveying information related to a current sleep stage of the subject during the current sleep session, and means for executing computer program modules. The computer program modules comprise means for determining the current sleep stage of the subject based on the output signals, the means for determining the current sleep stage configured to determine whether the subject is presently in slow wave sleep; means for determining individual time periods of slow wave sleep during the current sleep session based on the sleep stage determinations; means for controlling the means for providing sensory stimuli to provide the sensory stimuli to the subject during the individual time periods of slow wave sleep, the means for controlling configured to control the means for providing sensory stimuli to provide the sensory stimuli at a first intensity level during a first individual time period of slow wave sleep; means for determining an effectiveness of the provided sensory stimuli, the effectiveness being related to an increase in slow wave activity caused by the sensory stimuli, the effectiveness being determined based on the output signals, the means for determining an effectiveness configured to determine a first effectiveness of the sensory stimuli provided at the first intensity level during the first individual time period; and means for causing the means for providing sensory stimuli to increase the intensity of the provided sensory stimuli based on the determined effectiveness such that the intensity of the provided sensory stimuli is increased to a second intensity level based on the first effectiveness, wherein the means for determining an effectiveness and the means for causing are configured to repeat the effectiveness determination and the intensity increase one or more times during the individual time periods of slow wave sleep until expiration of the individual time periods such that the means for determining an effectiveness determines a second effectiveness of the sensory stimuli provided at the second intensity level during the first individual time period of slow wave sleep and the means for causing causes the means for providing sensory stimuli to increase the intensity of the provided sensory stimuli to a third intensity level. In some embodiments, the means for determining the current sleep stage is configured to determine one or more arousal levels of the subject during the individual time periods of slow wave sleep. The means for causing is configured to cause the means for providing sensory stimuli to decrease the intensity of, and/or cease providing, the sensory stimulation to the subject during a given period of slow wave sleep responsive to an arousal level determined by the means for determining the current sleep stage breaching an arousal level threshold during the given period of slow wave sleep These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
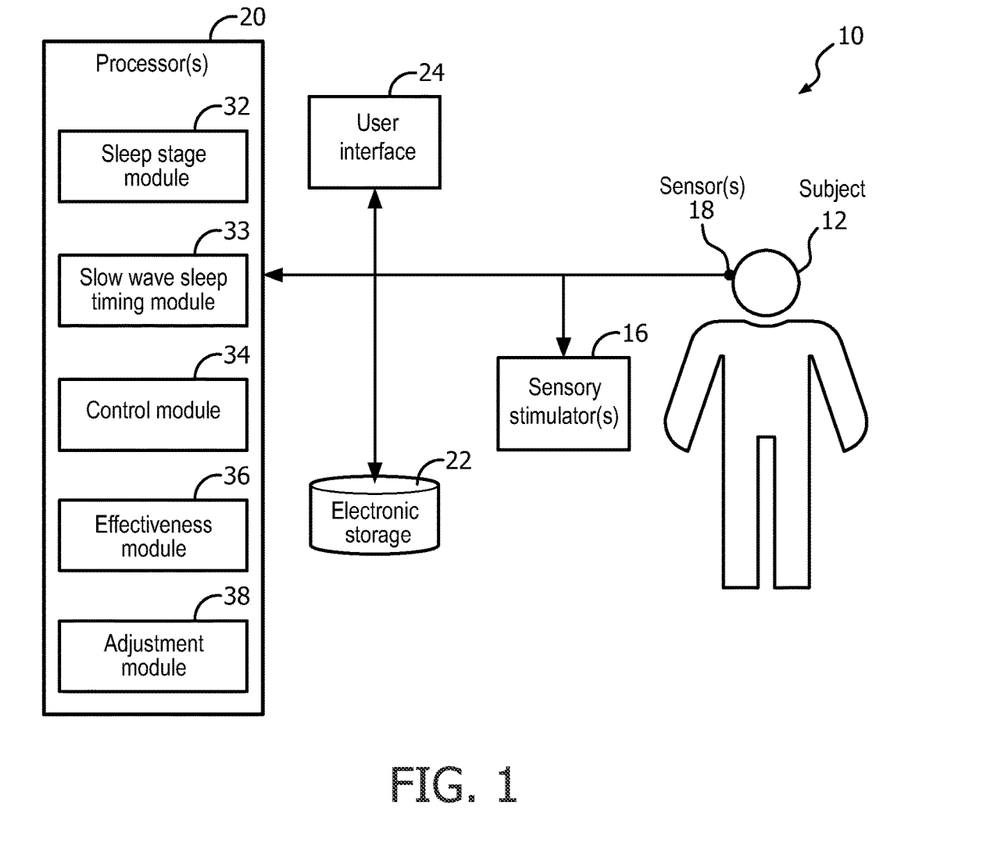
FIG. 1 is a schematic illustration of a system configured to manage a current sleep session of a subject.

FIG. 1 is a schematic illustration of a system 10 configured to manage a current sleep session of a subject 12. In some embodiments, system 10 may comprise one or more of a sensory stimulator 16, a sensor 18, a processor 20, electronic storage 22, a user interface 24, and/or other components. System 10 is configured such that a current sleep stage of subject 12 is determined one or more times during the sleep session. System 10 is configured to provide sensory stimuli to subject 12 during the current sleep session based on output signals generated by sensor 18. System 10 is configured such that the delivery of sensory stimulation during the current sleep session induces sleep slow waves and/or adjusts (e.g. enhance and/or decrease) slow wave activity (SWA) in subject 12. The manifestation of induced sleep slow waves may be measured through SWA. The delivery of the sensory stimulation is timed to correspond to sleep stages associated with SWA.

Sleep stages may include rapid eye movement (REM) sleep, and/or non-rapid eye movement (NREM) stage N1, stage N2, and/or stage N3 sleep. In some embodiments, stage N3 sleep may be and/or correspond to slow wave sleep. In some embodiments, stage N2 and/or stage N3 sleep may be slow wave sleep. In some embodiments, slow waves may not be present throughout the whole N3 period, for example, but it may be significantly more likely that such slow waves are present during N3. Slow waves may also be present (although to a lesser extent) during N2, for example.

Slow wave sleep and/or SWA may be observed and/or estimated by way of an electroencephalogram (EEG). In some embodiments, SWA corresponds to the power of the EEG signal in the 0.5-4.0 Hz band. In some embodiments, this band is set to 0.5-4.5 Hz. SWA has a typical behavior throughout cyclic variations of a given sleep session. SWA increases during NREM sleep, declines before the onset of REM sleep, and remains low during REM sleep. SWA in successive NREM (e.g., slow wave sleep) episodes progressively decreases from one episode to the next.

Figure 2:
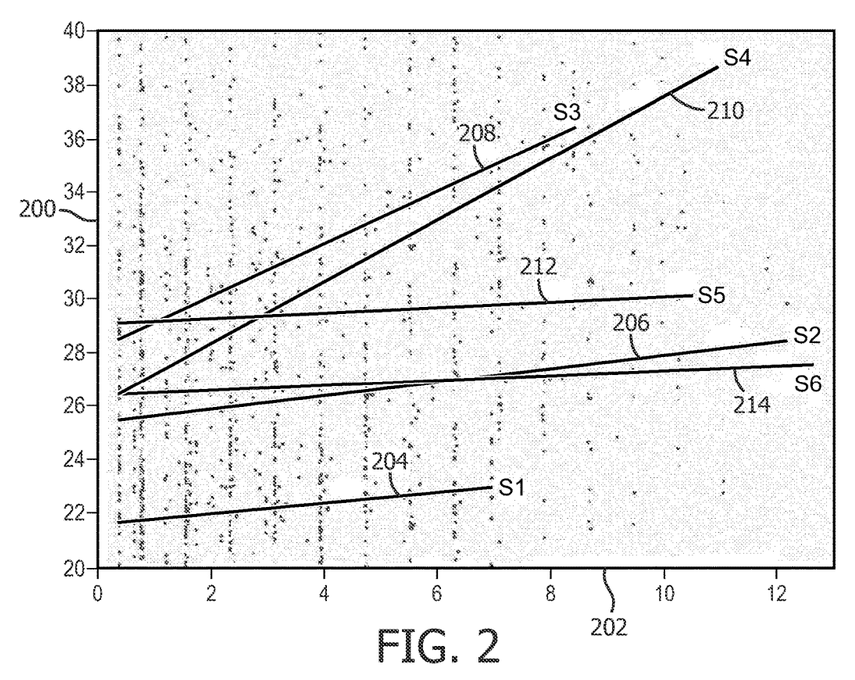
FIG. 2 illustrates experimental data from six subjects showing slow wave activity versus acoustic stimulation volume level.

Higher intensity sensory stimulation results in a higher level of SWA. For example, FIG. 2 illustrates experimental data from six subjects (S1-S6) showing SWA 200 versus acoustic stimulation volume level 202. The trend lines 204-214 show increasing SWA in each subject with increasing acoustic stimulation volume. However, starting the sensory stimulation at a high level risks waking the subjects. The system described herein is configured to incrementally increase the intensity of the sensory stimulation without waking subject 12 (shown in FIG. 1) from sleep.

Returning to FIG. 1, system 10 is configured to provide the sensory stimuli at a first intensity level, determine the effectiveness of the provided sensory stimuli, and increase the intensity level of the sensory stimuli based on the determined effectiveness. The effectiveness determination and the corresponding intensity increase are repeated one or more times during a given slow wave sleep episode. In some embodiments, system 10 is configured to continue the effectiveness determinations and the corresponding intensity increases during the given slow wave sleep episode until the intensity level reaches a maximum level. In some embodiments, system 10 is configured to continue the effectiveness determinations and the corresponding intensity increases during the given slow wave sleep episode until an arousal level of subject 12 breaches an arousal level threshold during the given period of slow wave sleep. In some embodiments, responsive to the intensity reaching the maximum level, system 10 is configured such that the intensity of the stimulation is no longer increased. In some embodiments, responsive to the arousal level breaching the arousal level threshold, system 10 is configured to cease providing the sensory stimuli to subject 12. In some embodiments, responsive to the intensity reaching the maximum level and/or the arousal level breaching the arousal level threshold, system 10 is configured to decrease the intensity of the sensory stimuli provided to subject 12.

Figure 3:
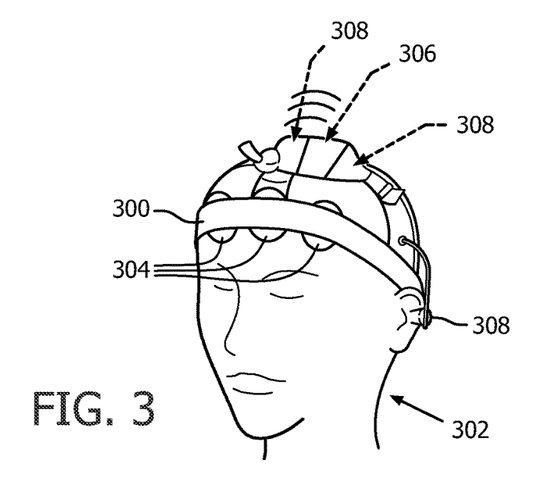
FIG. 3 illustrates a headset worn by a subject and includes sensing electrodes, a bio-signal amplifier, and a wireless audio device.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 3 illustrates a headset 300 worn by a subject 302 and includes sensing electrodes 304, a bio-signal amplifier 306, and a wireless audio device 308. Sensing electrodes 304 and bio-signal amplifier 306 may be represented, for example, by sensor 18 in FIG. 1. Wireless audio device 308 may be represented, for example, by sensory stimulator 16 shown in FIG. 1.

Returning to FIG. 1, sensory stimulator 16 is configured to provide sensory stimuli to subject 12. Sensory stimulator 16 is configured to provide sensory stimuli to subject 12 prior to the current sleep session, during the current sleep session, and/or at other times. For example, sensory stimulator 16 may be configured to provide sensory stimuli to subject 12 during slow wave sleep in the current sleep session. Sensory stimulator 16 may be configured to provide sensory stimuli to subject 12 during the current sleep session to induce sleep slow waves and/or adjust SWA in subject 12. In some embodiments, sensory stimulator 16 may be configured such that adjusting includes increasing (e.g., enhancing), decreasing, and/or other adjustment of SWA in subject 12.

In some embodiments, sensory stimulator 16 may be configured to induce sleep slow waves and/or adjust SWA through non-invasive brain stimulation and/or other methods. Sensory stimulator 16 may be configured to induce sleep slow waves and/or adjust SWA through non-invasive brain stimulation using the sensory stimuli. The sensory stimuli include odors, sounds, visual stimulation, touches, tastes, and/or other stimuli. For example, transcranial magnetic stimulation may be applied to subject 12 to trigger, increase, and/or decrease SWA. As another example, sensory stimulator 16 may be configured to induce sleep slow waves and/or adjust SWA via auditory stimulation of subject 12. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

In some embodiments, sensory stimulator 16 is configured to generate the sensory stimuli at one or more intensities. For example, sensory stimulator 16 may generate tones at a first lower decibel level and/or a second higher decibel level. In some embodiments, the one or more intensities may include the same sensory stimuli delivered at different timing intervals. For example, sensory stimulator 16 may generate tones at the first lower decibel level at a first lower frequency interval (first intensity level) and/or at a second higher frequency interval (second intensity level).

Sensor 18 is configured to generate output signals conveying information related to a current sleep stage of subject 12. Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to a current sleep stage of the subject indirectly. For example, one or more sensors 18 may generate an output based on a heart rate of subject 12 (e.g., sensor 18 may be a heart rate sensor located on the chest of subject 12, and/or be configured as an optical sensor included in a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), changes in skin color of subject 12 (e.g., sensor 18 may include a camera that can detect changes is skin color of subject 12 and infer vital signs such as heart rate, breathing rate, and/or other vital signs from the changes in color), respiration of subject 12, and/or other characteristics of subject 12. Although sensor 18 is illustrated at a single location in communication with subject 12, this is not intended to be limiting. Sensor 18 may include sensors disposed in a plurality of locations, such as for example, within (or in communication with) sensory stimulator 16, and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program modules. The one or more computer program modules may comprise one or more of a sleep stage module 32, a slow wave sleep timing module 33, a control module 34, an effectiveness module 36, an adjustment module 38, and/or other modules. Processor 20 may be configured to execute modules 32, 33, 34, 36, and/or 38 by software; hardware; firmware; some combination of software, hardware, and/or firmware; and/or other mechanisms for configuring processing capabilities on processor 20.

It should be appreciated that although modules 32, 33, 34, 36, and 38 are illustrated in FIG. 1 as being co-located within a single processing unit, in implementations in which processor 20 comprises multiple processing units, one or more of modules 32, 33, 34, 26, and/or 38 may be located remotely from the other modules. The description of the functionality provided by the different modules 32, 33, 34, 36, and/or 38 described below is for illustrative purposes, and is not intended to be limiting, as any of modules 32, 33, 34, 36, and/or 38 may provide more or less functionality than is described. For example, one or more of modules 32, 33, 34, 36, and/or 38 may be eliminated, and some or all of its functionality may be provided by other modules 32, 33, 34, 36, and/or 38. As another example, processor 20 may be configured to execute one or more additional modules that may perform some or all of the functionality attributed below to one of modules 32, 33, 34, 36, and/or 38.

Sleep stage module 32 is configured to determine the current sleep stage of subject 12 based on the output signals of sensor 18. As described above, the current sleep stage of subject 12 may correspond to one or more of wakefulness, REM sleep, stage N1, stage N2, and/or stage N3 sleep. Sleep stage module 32 is configured to determine whether subject 12 is presently in slow wave sleep. In some embodiments, slow wave sleep and/or slow wave activity may correspond to stage N3 sleep. In some embodiments, stage N2 and/or stage N3 sleep may be slow wave sleep and/or correspond to slow wave activity.

In some embodiments, sleep stage module 32 may determine the current sleep stage of subject 12 based on an analysis of the information conveyed by the output signals of sensor 18. The analysis may include generating and/or monitoring an EEG during the sleep session of subject 12. In some embodiments, the analysis may include detecting slow wave sleep based on a power in a delta band and/or a power in a beta band of the EEG. The power in the delta band is usually defined as the power in the frequency range 0.5-4.5 Hz although there is no standard definition of the frequency limits. The power in the beta band is usually defined as the power in the frequency range 15-30 Hz although variations in limits of the range are very common.

In some embodiments, sleep stage module 32 is configured to determine one or more arousal levels of the subject during the current sleep session. The one or more arousal levels may indicate a level of wakefulness in subject 12. The one or more arousal levels may be determined based on the output signals of sensor 18, information stored in electronic storage 22, testing performed prior to the current sleep session, information received and/or selected via user interface 24, and/or other information. In some embodiments, the one or more arousal levels may be determined based on the analysis of the information related to the EEG. For example, the likelihood for an arousal may be quantified from the EEG power in the beta band in short temporal windows (typically about 1.5 second long, for example). Responsive to the power in the beta band exceeding a predefined threshold, system 10 may decide that an arousal is present. In some embodiments, the beta band power threshold for arousals may be determined based on a previous sleep session of subject 12, based on information related a population of subjects demographically similar to subject 12, and/or based on other information. For example, the beta band power threshold may be determined based on a calibration night of sleep during which the EEG of subject 12 is measured and the statistics of the beta power throughout the sleep session are analyzed to set the threshold. As another example, the beta band power threshold may be determined via a database containing the beta thresholds for a population of subjects. The beta band power threshold for subject 12 may be determined based on demographically matching subject 12 with subjects present in the database.

Slow wave sleep timing module 33 is configured to determine individual time periods of slow wave sleep in subject 12 during the current sleep session. Slow wave sleep timing module 33 is configured to determine the individual time periods of slow wave sleep based on the sleep stage determinations (e.g., whether subject 12 is presently in slow wave sleep) by sleep stage module 32. For example, slow wave sleep timing module 33 may determine a first individual time period of slow wave sleep such that the start of the first individual time period coincides with the start of a first slow wave sleep episode during the current sleep session and/or stops with the end of the first slow wave sleep episode (e.g., sleep stage module 32 determines that subject 12 is no longer in slow wave sleep). The start of a second individual time period of slow wave sleep may coincide with the start of a second episode of slow wave sleep during the current sleep session and/or stops with the end of the second slow wave sleep episode.

In some embodiments, slow wave sleep timing module 33 is configured to determine the individual time periods such that the individual time periods begin a predetermined amount of time after sleep stage module 32 determines that subject 12 is presently in slow wave sleep. In some embodiments, slow wave sleep timing module 33 is configured to determine the individual time periods such that the individual time periods end a predetermined amount of time after sleep stage module 32 determines that subject 12 is presently in slow wave sleep. In some embodiments, the one or more predetermined amounts of time may be based on typical amounts of time between the beginning of slow wave sleep and the end of a slow wave sleep for a given episode of slow wave sleep during the current sleep session. The typical amounts of time may be determined based on a current sleep session of subject 12, previous sleep sessions of subject 12, and/or other sleep sessions. In some embodiments, the one or more predetermined amounts of time may be programmed at manufacture, set by a user via user interface 24, and/or determined by other methods.

In some embodiments, sleep stage module 32 may determine the one or more arousal levels during the individual time periods of slow wave sleep. In some embodiments, slow wave sleep timing module 33 may determine the end of a given individual time period of slow wave sleep based on the arousal levels determined by sleep stage module 32.

Control module 34 is configured to control sensory stimulator 16 to provide the sensory stimuli to subject 12 during the individual time periods of slow wave sleep (e.g., during stage N3 sleep). In some embodiments, the timing for delivery of sensory stimulation may correspond to the determination that subject 12 is presently in slow wave sleep. Control module 34 may be configured to control sensory stimulator 16 to provide the sensory stimuli to subject 12 such that the provided sensory stimuli corresponds to sleep stages associated with slow wave activity because the likelihood for slow-wave induction, and/or adjustment during the specific sleep stage may be comparatively higher than in other sleep stages, the user may be less likely to be awakened by the sensory stimuli, and/or for other reasons.

In some embodiments, control module 34 is configured to control sensory stimulator 16 to provide the sensory stimuli in the form of auditory tones that are brief in duration (e.g., about 50 ms long), have a predetermined frequency, and are separated from each other by an inter-tone-interval. In some embodiments, one or more of the auditory tone duration, the predetermined frequency, the inter-tone-interval, and/or other characteristics of the sensory stimuli may be programmed at manufacture, set by a user via user interface 24, determined by system 10 based on previous sleep sessions of subject 12, determined based on the current sleep session, and/or determined by other methods.

In some embodiments, control module 34 is configured to control sensory stimulator 16 to provide the sensory stimuli (e.g., auditory tones) to subject 12 such that habituation in subject 12 is avoided. Habituation is a decrease of a response (e.g., behavioral and/or cortical) to a repeated eliciting stimulus not due to fatigue. Habituation to repetitive sensory stimuli manifests itself as a reduction in amplitude of the cortical response as determined via the EEG. Habituation may adversely affect SWA induction, and/or adjustment (e.g., enhancement) caused by system 10. Control module 34 may be configured to randomize the frequency of the sensory stimuli to counter habituation.

Control module 34 is configured to control sensory stimulator 16 to provide the sensory stimuli at a first intensity level during the first individual time period of slow wave sleep. Control module 34 may be configured to control sensory stimulator 16 to increase the intensity of the sensory stimuli to the first intensity level relative to a baseline intensity level. The baseline intensity level may be the intensity level of ambient sensory stimuli in a room where the subject is sleeping (e.g. noise from automobile traffic outside the room, lighting, etc.). In some embodiments, control module 34 may control sensory stimulator 16 to provide sensory stimuli at a baseline intensity level. The baseline intensity level may be zero intensity (e.g., no sensory stimulation is provided by sensory stimulator 16) and/or may be an amount of sensory stimulation determined based on the current and/or previous sleep sessions of the subject, and/or other information, for example.

Control module 34 is configured to control sensory stimulator 16 to provide the sensory stimuli at the first intensity level such that the sensory stimulation does not wake subject 12. Control module 34 is configured such that the first intensity level is determined based on previous sleep sessions of subject 12, testing performed on subject 12 during wakefulness, and/or other information. In some embodiments, the first intensity level may be the lowest intensity subject 12 is able to perceive during wakefulness, for example. Information related to the intensity of stimulation during previous sleep sessions of subject 12 and/or testing performed on subject 12 during wakefulness may be stored in electronic storage 22, for example. In some embodiments, control module 34 may cause information related to the current sleep session of subject 12 to be stored in electronic storage 22. Information related to the current sleep session may include information related to the intensity level of the sensory stimulation, sleep stage information, timing information, and/or other information.

Effectiveness module 36 is configured to determine an effectiveness of the provided sensory stimuli. The effectiveness is related to an increase in SWA caused by the provided sensory stimuli. The effectiveness is determined based on the output signals of sensor 18, information related to the EEG of subject 12 during the current sleep session, and/or other information. For example, effectiveness module 36 is configured to determine a first effectiveness of the sensory stimuli provided at the first intensity level during the first individual time period. In some embodiments, effectiveness module 36 is configured to determine the effectiveness of the provided sensory stimuli based on the SWA in subject 12 during a window of time just after the sensory stimulation is delivered to subject 12 at the first intensity level by sensory stimulator 16. In some embodiments, the effectiveness is determined by comparing the SWA in a window of time just before the stimulation to the SWA in a window of time just after the stimulation.

Adjustment module 38 is configured to cause sensory stimulator 16 to increase the intensity of the provided sensory stimuli based on the intensity of sensory stimuli previously provided to subject 12, the determined effectiveness, the EEG power in the spindle band (e.g., 11-15 Hz), a prediction of the effectiveness, and/or other information. For example, adjustment module 38 may cause the intensity of the provided sensory stimuli to increase to a second intensity level based on the first effectiveness. Adjustment module 38 may be configured such that an increase in the intensity of sensory stimulation is based on information determined via the EEG (e.g., by sleep stage module 32). In some embodiments, adjustment module 38 is configured such that an increase in the intensity of sensory stimulation is based on information determined by adjustment module 38 via an algorithm. Algorithm inputs may include the determined effectiveness, information related to a predicted SWA enhancement determined via information related to the EEG, information related to a spindle rate/density determined via the EEG, and/or other information. In some embodiments, the EEG power in the spindle band (e.g., about 11 to 15 Hz) may be used to detect sleep spindles and estimate the spindle rate/density (spindles/minute). A higher spindle rate/density indicates a higher arousal threshold in relation to external stimulation. If the spindle rate/density is high, then the increase in the stimulation intensity may be larger than it would be if the spindle rate/density were low. In some embodiments, a prediction of the effectiveness may be obtained by adjustment module 38 via fitting a curve to the sleep slow waves and extrapolating the result to the time instants where the stimulation is delivered.

In some embodiments, effectiveness module 36 and/or adjustment module 38 are configured to repeat the effectiveness determination and the intensity increase one or more times during the individual time periods of slow wave sleep such that the intensity level of the sensory stimulation is incrementally increased during the individual time periods of slow wave sleep. Effectiveness module 36 and/or adjustment module 38 are configured to repeat the effectiveness determination and the intensity increase one or more times until expiration of the individual time periods. For example, effectiveness module 36 may determine a second effectiveness of the sensory stimuli provided at the second intensity level during the first individual time period of slow wave sleep and adjustment module 38 may cause sensory stimulator 16 to increase the intensity of the provided sensory stimuli to a third intensity level.

In some embodiments, adjustment module 38 is configured to cause sensory stimulator 16 to increase the intensity level one or more times during a given time period of slow wave sleep until the intensity level reaches a maximum level. In some embodiments, the maximum intensity level may be obtained by adjustment module 38 responsive to testing performed on subject 12 during wakefulness prior to the current sleep session. In some embodiments, the maximum intensity level may be obtained by adjustment module 38 responsive to user interface 24 receiving entry and/or selection of information related to the maximum intensity level. In some embodiments, adjustment module 38 is configured to determine the maximum intensity level based on the current sleep session of subject 12 and/or previous sleep sessions of subject 12.

In some embodiments, adjustment module 38 is configured to cause sensory stimulator 16 to cease providing the sensory stimuli to subject 12 during a given period of slow wave sleep responsive to an arousal level determined by sleep stage module 32 breaching an arousal level threshold during the given period of slow wave sleep. In some embodiments, adjustment module 38 is configured to cause sensory stimulator 16 to decrease the intensity of the sensory stimuli provided to subject 12 responsive to the arousal level of the subject breaching the arousal level threshold.

The arousal level threshold may be determined by sleep stage module 32 based on information related to the current sleep session, information related to a previous sleep session, and/or other information. In some embodiments, the arousal level threshold may be obtained by sleep stage module 32 responsive to testing performed on subject 12 during wakefulness prior to the current sleep session. In some embodiments, the arousal level threshold may be determined by sleep stage module 32 responsive to user interface 24 receiving entry and/or selection of information related to the arousal level threshold.

In some embodiments, incrementally increasing the intensity level of the sensory stimulation may increase the arousal level threshold for subject 12. For example, an arousal level threshold determined for auditory stimulation of subject 12 during testing prior to the current sleep session may indicate that subject 12 wakes from sleep responsive to sound at a first decibel level. Subject 12 may wake from sleep at a second higher decibel level during the current sleep session responsive to the intensity of the sensory stimulation being incrementally increased by system 10 during the current sleep session as described herein.

Figure 4:
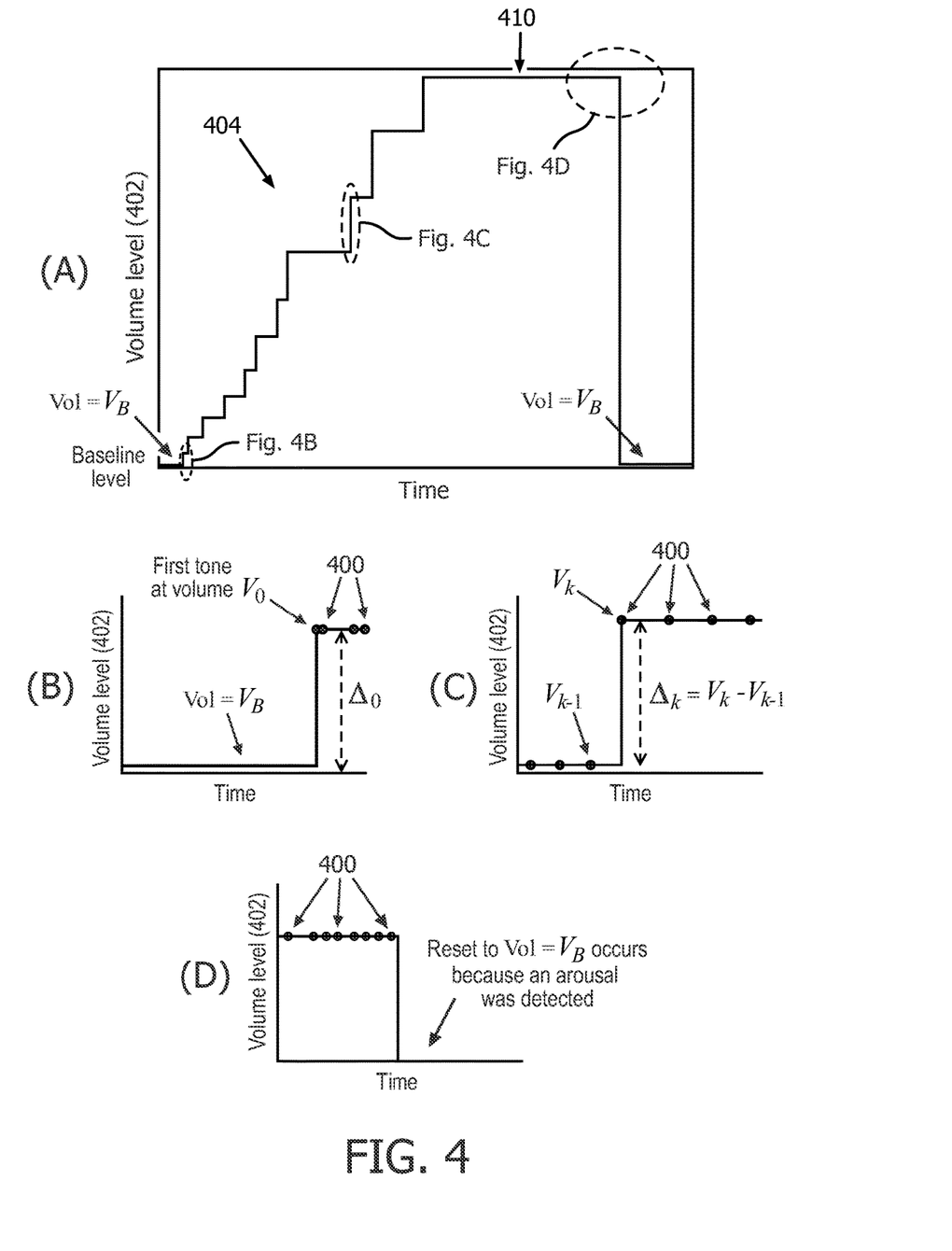
FIG. 4 illustrates acoustic stimulation delivered to a subject in the form of auditory tones.

FIG. 4 illustrates acoustic stimulation delivered to a subject in the form of auditory tones 400 (e.g. by sensory stimulator 16 shown in FIG. 1). FIG. 4 illustrates an example of at least some of the functionality of sensory stimulator 16 (shown in FIG. 1), sleep stage module 32 (FIG. 1), slow wave sleep timing module 33 (FIG. 1), control module 34 (FIG. 1), effectiveness module 36 (FIG. 1), adjustment module 38 (FIG. 1), and/or other components of system 10. The volume (intensity) 402 of the acoustic tones is incrementally increased 404 (FIG. 4A) based on the effectiveness of previous tones at enhancing SWA in the subject. The tones may have a duration, a frequency, an inter-tone-interval, and/or other characteristics. The tones may be generated for the subject while the subject is sleeping in an environment having a baseline volume, $V_B$. The baseline volume level may be the ambient volume in a room where the subject is sleeping, for example. In some embodiments, control module 34 may control sensory stimulator 16 to provide noise at a baseline volume level. The baseline volume level may be zero volume, may be determined based on the current and/or previous sleep sessions of the subject, and/or include other volumes.

The volume of the first tone (e.g., determined by control module 34), $V_0$ (FIG. 4B), may be determined based on previous sleep sessions of subject 12, testing performed on subject 12 during wakefulness, and/or other information. In some embodiments, the first tone volume may be the lowest volume the subject is able to hear during wakefulness, for example. The first incremental increase, $\Delta_0$, may be equal to $V_0-V_B$, for example.

The volume of the k-th tone (FIG. 4C), $V_k$, may be determined (e.g., by adjustment module 38) based on the volume of the previous tone using $V_k=V_{k-1}+\Delta_k$, where $\Delta_k$ is the incremental increase at the k-th tone. The incremental increase, $\Delta_k$, may be determined based on the estimated effectiveness (e.g., determined by effectiveness module 36) in enhancing SWA after delivering the (k−1)-th tone, information related to an EEG of the subject (e.g., determined by sleep stage module 32), and/or other information. For example, the incremental increase may be determined based on the equation $\Delta_k$ ($E_{SWA}$, $P_{SWA}$, $\sigma_r$), where $E_{SWA}$ is an estimated effectiveness in enhancing SWA in the subject after the k-th tone has been delivered, $P_{SWA}$ is a prediction of the SWA enhancement following the k-th tone, and $\sigma_r$ is a spindle rate.

The estimated effectiveness in enhancing SWA after the k-th tone has been delivered, $E_{SWA}$, may be, for example, a ratio between the SWA in a time window lasting for T seconds between the time instants $t_k+\tau-T$ and $t_k+\tau$ (where $t_k$ is the time at which the k-th tone was delivered and τ>0) and the SWA in a time window lasting for 2T seconds between the time instants $t_k+\tau-3T$ and $t_k+\tau-T$. In some embodiments, T is a constant having a value of about 500 milliseconds, for example, and τ is a constant having a value of about 200 milliseconds, for example. Because τ seconds are considered after delivery of the k-th tone, the influence of this stimulation may be taken into account to determine the effectiveness of the SWA enhancement. The values given here for T and τ are not intended to be limiting. T and/or τ may have and/or be assigned values such that the influence of the current stimulation (delivered at $t_k$) is taken into account.

The prediction of the SWA enhancement following the k-th tone, $P_{SWA}$, may be determined based on tracking the induced sleep slow waves using a phase-locked-loop (PLL) approach, for example, and predicting the phase of the future sleep slow waves. Based on the PLL approach, system 10 may be configured such that a sinusoidal curve at a frequency of 1 Hz, for example, is fit to the sleep slow waves. Sleep stage module 32, control module 34, effectiveness module 36 and/or adjustment module 38 may be configured such that the fit is performed in real-time. Based on the fit, system 10 may predict when (with respect to the sleep slow wave) the acoustic tone is to be delivered. For example, system 10 may be configured such that the acoustic tone is delivered in the vicinity of the negative peak of the sleep slow wave.

The spindle rate, $\sigma_r$, may be determined based on a sleep spindle that is determined via the EEG. The sleep spindle is a thalamocortical rhythm manifested on the EEG as a brief 11-15 Hz oscillation and is thought to be capable of modulating the influence of external stimuli. The robustness of sleep in the face of acoustic stimulation may be predicted from the spindle rate. A higher spindle rate/density indicates a higher robustness of sleep is in the presence of acoustic stimulation. The spindle rate may be considered high responsive to the spindle rate exceeding 5 spindles per minute, for example. In the case of a high spindle rate, the incremental increase, $\Delta_k$, may be increased by about 20% from the previous intensity, for example.

As shown in FIG. 4D, responsive to an arousal level of the subject (e.g., determined by sleep stage module 32) breaching (e.g., determined by adjustment module 38) an arousal level threshold (e.g., determined by sleep stage module 32), the sensory stimulation is stopped and the volume is reset to the baseline level (e.g., by adjustment module 38). Responsive to the subject entering a subsequent time period of slow wave sleep (e.g., determined by slow wave sleep timing module 33), the process of incrementally increasing the intensity of the sensory stimulation restarts.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. For example, electronic storage 22 may store information related to the intensity levels of the sensory stimulation provided to subject 12 during previous sleep sessions and/or the current sleep session. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or the other users may provide information to and receive information from system 10. Other users may include doctors, caregivers, and/or other users. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 5:
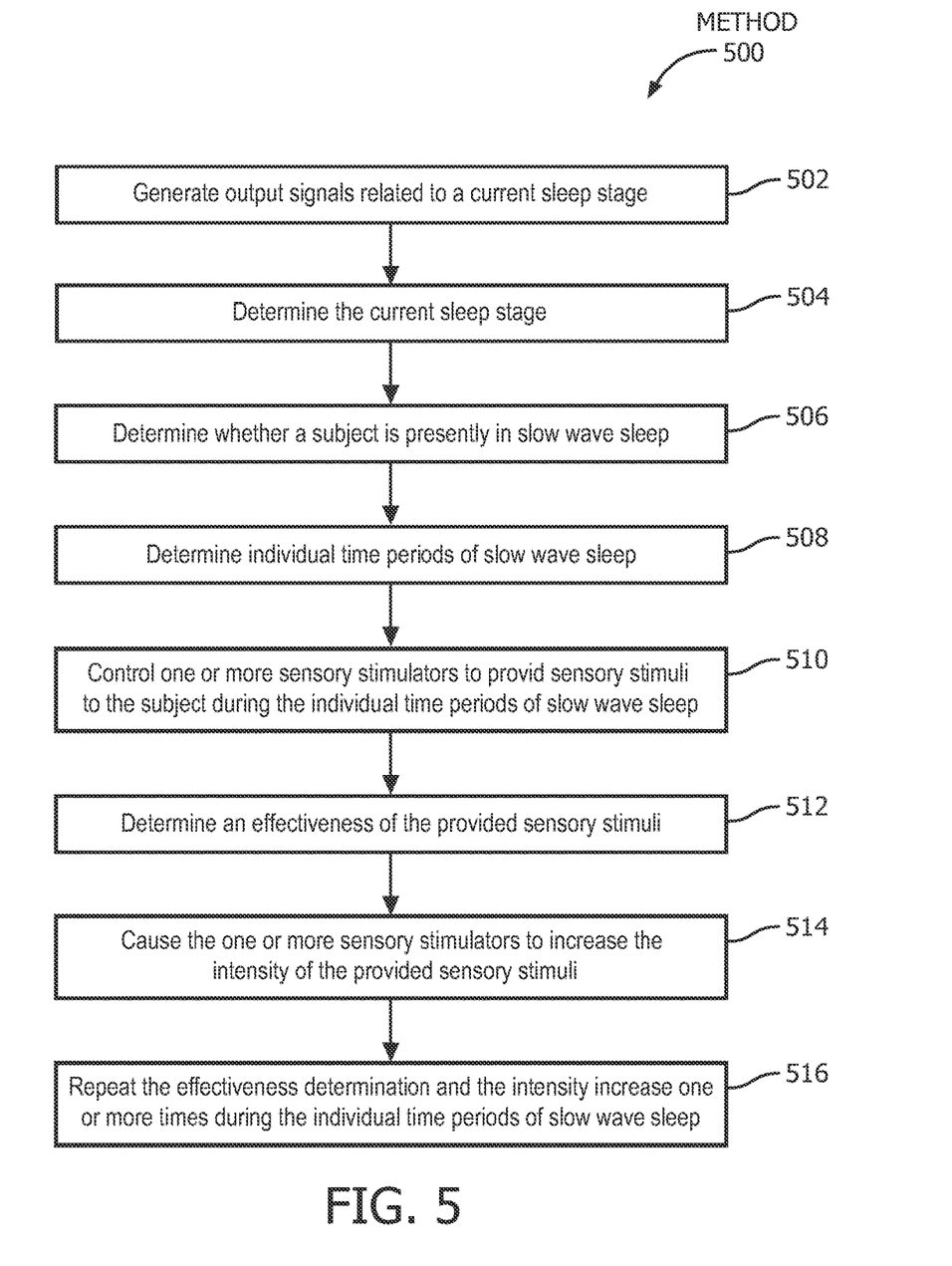
FIG. 5 illustrates a method for managing a current sleep session of a subject with a management system.

FIG. 5 illustrates a method 500 for managing a current sleep session of a subject with a management system. The system comprises one or more sensory stimulators, one or more sensors, and one or more processors configured to execute computer program modules. The computer program modules comprise a sleep stage module, a slow wave sleep timing module, a control module, an effectiveness module, and an adjustment module. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, output signals conveying information related to a current sleep stage of the subject during the current sleep session are generated. In some embodiments, operation 502 is performed by one or more sensors the same as or similar to sensors 18 (shown in FIG. 1 and described herein).

At an operation 504, the current sleep stage of the subject is determined based on the output signals. In some embodiments, operation 504 is performed by a computer program module the same as or similar to sleep stage module 32 (shown in FIG. 1 and described herein).

At an operation 506, whether the subject is presently in slow wave sleep is determined. Whether the subject is presently in slow wave sleep is determined based on the sleep stage determinations. In some embodiments, slow wave sleep may be stage N3 sleep. In some embodiments, operation 506 is performed by a computer program module the same as or similar to sleep stage module 32 (shown in FIG. 1 and described herein).

At an operation 508, individual time periods of slow wave sleep during the current sleep session are determined. The individual time periods of slow wave sleep are determined based on the sleep stage determinations. In some embodiments, operation 508 is performed by a computer program module the same as or similar to slow wave sleep timing module 33 (shown in FIG. 1 and described herein).

At an operation 510, the one or more sensory stimulators are controlled to provide sensory stimuli to the subject during the individual time periods of slow wave sleep. The controlling includes controlling the one or more sensory stimulators to provide the sensory stimuli at a first intensity level during a first individual time period of slow wave sleep. In some embodiments, the first intensity level may be determined based on previous sleep sessions of the subject. In some embodiments, operation 510 is performed by a computer program module the same as or similar to control module 34 (shown in FIG. 1 and described herein).

At an operation 512, an effectiveness of the provided sensory stimuli is determined. The effectiveness is related to an increase in slow wave activity caused by the sensory stimuli. The effectiveness is determined based on the output signals. A first effectiveness of the sensory stimuli provided at the first intensity level during the first individual time period is determined. In some embodiments, operation 512 is performed by a computer program module the same as or similar to effectiveness module 36 (shown in FIG. 1 and described herein).

At an operation 514, the one or more sensory stimulators are caused to increase the intensity of the provided sensory stimuli. The increase is based on the determined effectiveness. The intensity of the provided sensory stimuli is increased to a second intensity level based on the first effectiveness, and/or other information. In some embodiments, the increase in the intensity of sensory stimulation is based on information determined via an algorithm. Algorithm inputs may include the determined effectiveness, information related to a predicted SWA enhancement determined via information related to the EEG, information related to a spindle rate/density determined via the EEG, and/or other information. In some embodiments, the EEG power in the spindle band (e.g., about 11 to 15 Hz) may be used to detect sleep spindles and estimate the spindle rate/density (spindles/minute). A higher spindle rate/density indicates a higher arousal threshold in relation to external stimulation. If the spindle rate/density is high, then the increase in the stimulation intensity may be larger than it would be if the spindle rate/density were low. In some embodiments, a prediction of the effectiveness may be obtained via fitting a curve to the sleep slow waves and extrapolating the result to the time instants where the stimulation is delivered. In some embodiments, operation 514 is performed by a computer program module the same as or similar to adjustment module 38 (shown in FIG. 1 and described herein).

At an operation 516, the effectiveness determination and then the intensity increase are repeated one or more times during the individual time periods of slow wave sleep. The effectiveness determination and the intensity increase are repeated one or more times until expiration of the individual time periods. For example, a second effectiveness of the sensory stimuli provided at the second intensity level during the first individual time period of slow wave sleep is determined and the one or more sensory stimulators are caused to increase the intensity of the provided sensory stimuli to a third intensity level. In some embodiments, the intensity level may be increased one or more times until the intensity reaches a maximum level. In some embodiments, the sensory stimulators may be caused to cease providing the sensory stimuli during a given period of slow wave sleep responsive to an arousal level of the subject breaching an arousal level threshold during the given period of slow wave sleep. In some embodiments, the sensory stimulators may be caused to decrease the intensity of the sensory stimulation during a given period of slow wave sleep responsive to the arousal level of the subject breaching the arousal level threshold during the given period of slow wave sleep. In some embodiments, operation 516 is performed by computer program modules the same as or similar to sleep stage module 32, effectiveness module 36, and/or adjustment module 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to manage a current sleep session of a subject, the system comprising:
   one or more sensory stimulators configured to provide sensory stimuli o the subject;
   one or more sensors configured to generate output signals conveying information related to a current sleep stage of the subject during the current sleep session; and
   one or more processors configured to execute computer program modules, the computer program modules comprising:
   a sleep stage module configured to determine the current sleep stage of the subject based on the output signals, the sleep stage module configured to determine whether the subject is presently in slow wave sleep;

a slow wave sleep timing module configured to determine individual time periods of slow wave sleep during the current sleep session based on the sleep stage determinations by the sleep stage module;

a control module configured to control the one or more sensory stimulators to provide the sensory stimuli to the subject during the individual time periods of slow wave sleep, the control module configured to control the one or more sensory stimulators to provide the sensory stimuli at a first intensity level during a first individual time period of slow wave sleep;

an effectiveness module configured to determine an effectiveness of the provided sensory stimuli, the effectiveness being related to an increase in slow wave activity caused by the sensory stimuli, the effectiveness being determined based on the output signals, the effectiveness module configured to determine a first effectiveness of the sensory stimuli provided at the first intensity level during the first individual time period of slow wave sleep; and an adjustment module configured to cause the one or more sensory stimulators to increase the first intensity level of the provided sensory stimuli based on the determined effectiveness such that the first intensity level of the provided sensory stimuli is increased by a first amount to a second intensity level based on the first effectiveness, wherein the effectiveness module and the adjustment module are configured to repeat the effectiveness determination and the intensity increase one or more times during the individual time periods of slow wave sleep until expiration of the individual time periods such that the effectiveness module determines at least a second effectiveness of the sensory stimuli provided at the second intensity level during the first individual time period of slow wave sleep and the adjustment module causes the one or more sensory stimulators to increase the second intensity level of the provided sensory stimuli by a second amount to a third intensity level.

2. The system of claim 1, wherein the sleep stage module is configured to determine one or more arousal levels of the subject during the individual time periods of slow wave sleep, and wherein the adjustment module is configured to cause the sensory stimulators to cease providing the sensory stimulation to the subject during a given period of slow wave sleep responsive to an arousal level determined by the sleep stage module breaching an arousal level threshold during the given period of slow wave sleep, the arousal level threshold determined by the sleep stage module based on one or more of the current sleep session, a previous sleep session of the subject, or information related to previous sleep sessions of other people, the other people corresponding demographically to the subject.

3. The system of claim 1, wherein the sleep stage module is configured to determine one or more arousal levels of the subject during the individual time periods of slow wave sleep, and wherein the adjustment module is further configured to cause the one or more sensory stimulators to decrease the intensity of the sensory stimulation provided to the subject responsive to the arousal level of the subject breaching an arousal level threshold, the arousal level threshold determined by the sleep stage module based on one or more of the current sleep session, a previous sleep session of the subject, or information related to previous sleep sessions of other people, the other people corresponding demographically to the subject.

4. The system of claim 1, wherein the adjustment module is configured to cause the sensory stimulators to increase the intensity level during a given time period of slow wave sleep until the intensity level reaches a maximum level.

5. The system of claim 1, wherein the control module is configured such that the first intensity level is determined based on previous sleep sessions of the subject.

6. The system of claim 1, wherein the adjustment module is configured such that the first amount and the second amount are different.

7. The system of claims 6, wherein the adjustment module is configured such that the first amount and the second amount are determined during the first individual period of slow wave sleep.

8. A method for managing a current sleep session of a subject with a management system, the system comprising one or more sensory stimulators, one or more sensors, and one or more processors configured to execute computer program modules, the computer program modules comprising a sleep stage module, a slow wave sleep timing module, a control module, an effectiveness module, and an adjustment module, the method comprising:

generating, with the one or more sensors, output signals conveying information related to a current sleep stage of the subject during the current sleep session;

determining, with the sleep stage module, the current sleep stage of the subject based on the output signals;

determining, with the sleep stage module, whether the subject is presently in slow wave sleep based on the sleep stage determinations;

determining, with the slow wave sleep timing module, individual time periods of slow wave sleep during the current sleep session based on the sleep stage determinations;

controlling, with the control module, the one or more sensory stimulators to provide sensory stimuli to the subject during the individual time periods of slow wave sleep, the controlling including controlling the one or more sensory stimulators to provide the sensory stimuli at a first intensity level during a first individual time period of slow wave sleep;

determining, with the effectiveness module, an effectiveness of the provided sensory stimuli, the effectiveness being related to an increase in slow wave activity caused by the sensory stimuli, the effectiveness being determined based on the output signals such that a first effectiveness of the sensory stimuli provided at the first intensity level during the first individual time period of slow wave sleep is determined;

causing, with the adjustment module, the one or more sensory stimulators to increase the first intensity level of the provided sensory stimuli based on the determined effectiveness such that the first intensity level of the provided sensory stimuli is increased by a first amount to a second intensity level based on the first effectiveness; and repeating, with the effectiveness module and the adjustment module, the effectiveness determination and the intensity increase one or more times during the individual time periods of slow wave sleep until expiration of the individual time periods such that a second effectiveness of the sensory stimuli provided at the second intensity level during the first individual time period of slow wave sleep is determined and the one or more sensory stimulators are caused to increase the second intensity level of the provided sensory stimuli by a second amount to a third intensity level.

9. The method of claim 8, further comprising determining, with the sleep stage module, one or more arousal levels of the subject during the individual time periods of slow wave sleep, and causing, with the adjustment module, the sensory stimulators to cease providing the sensory stimulation to the subject during a given period of slow wave sleep responsive to an arousal level breaching an arousal level threshold during the given period of slow wave sleep, the arousal level threshold determined by the sleep stage module based on one or more of the current sleep session, a previous sleep session of the subject, or information related to previous sleep sessions of other people, the other people corresponding demographically to the subject.

10. The method of claim 8, further comprising determining, with the sleep stage module, one or more arousal levels of the subject during the individual time periods of slow wave sleep, and causing, with the adjustment module, the one or more sensory stimulators to decrease the intensity of the sensory stimulation provided to the subject responsive to the arousal level of the subject breaching an arousal level threshold, the arousal level threshold determined by the sleep stage module based on one or more of the current sleep session, a previous sleep session of the subject, or information related to previous sleep sessions of other people, the other people corresponding demographically to the subject.

11. The method of claim 8, further comprising causing, with the adjustment module, the sensory stimulators to increase the intensity level during a given time period of slow wave sleep until the intensity level reaches a maximum level.

12. The method of claim 8, further comprising determining the first intensity level based on previous sleep sessions of the subject.

13. The method of claim 8 wherein the first amount and the second amount are different.

14. The method of claim 13, wherein the first amount and the second amount determined during the first individual period of slow wave sleep.

15. A system configured to manage a current sleep session of a subject, the system comprising:
  means for providing sensory stimuli to the subject;
  means for generating output signals conveying information related to a current sleep stage of the subject during the current sleep session; and
  means for executing computer program modules, the computer program modules comprising:
    means for determining the current sleep stage of the subject based on the output signals, the means for determining the current sleep stage configured to determine whether the subject is presently in slow wave sleep;
    means for determining individual time periods of slow wave sleep during the current sleep session based on the sleep stage determinations;
    means for controlling the means for providing sensory stimuli to provide the sensory stimuli to the subject during the individual time periods of slow wave sleep, the means for controlling configured to control the means for providing sensory stimuli to provide the sensory stimuli at a first intensity level during a first individual time period of slow wave sleep;
    means for determining an effectiveness of the provided sensory stimuli, the effectiveness being related to an increase in slow wave activity caused by the sensory stimuli, the effectiveness being determined based on the output signals, the means for determining an effectiveness configured to determine a first effectiveness of the sensory stimuli provided at the first intensity level during the first individual time period of slow wave sleep; and
    means for causing the means for providing sensory stimuli to increase the first intensity level of the provided sensory stimuli based on the determined effectiveness such that the first intensity level of the provided sensory stimuli is increased by a first amount to a second intensity level based on the first effectiveness,
    wherein the means for determining an effectiveness and the means for causing are configured to repeat the effectiveness determination and the intensity increase one or more times during the individual time periods of slow wave sleep until expiration of the individual time periods such that the means for determining an effectiveness determines a second effectiveness of the sensory stimuli provided at the second intensity level during the first individual time period of slow wave sleep and the means for causing causes the means for providing sensory stimuli to increase the second intensity level of the provided sensory stimuli by a second amount to a third intensity level.

16. The system of claim 15, wherein the means for determining the current sleep stage is configured to determine one or more arousal levels of the subject during the individual time periods of slow wave sleep, and wherein the means for causing is configured to cause the means for providing sensory stimuli to cease providing the sensory stimulation to the subject during a given period of slow wave sleep responsive to an arousal level determined by the means for determining the current sleep stage breaching an arousal level threshold during the given period of slow wave sleep, the arousal level threshold determined by the means for determining the current sleep stage based on one or more of the current sleep session, a previous sleep session of the subject, or information related previous sleep sessions of other people, the other people corresponding demographically to the subject.

17. The system of claim 15, wherein the means for determining the current sleep stage is configured to determine one or more arousal levels of the subject during the individual time periods of slow wave sleep, and wherein the means for causing is configured to cause the means for providing sensory stimuli to decrease the intensity of the sensory stimulation provided to the subject responsive to the arousal level of the subject breaching an arousal level threshold, the arousal level threshold determined by the means for determining the current sleep stage based on one or more of the current sleep session, a previous sleep session of the subject, or information related to previous sleep sessions of other people, the other people corresponding demographically to the subject.

18. The system of claim 15, wherein the means for causing is configured to cause the means for providing sensory stimuli to increase the intensity level during a given time period of slow wave sleep until the intensity level reaches a maximum level.

19. The system of claim 15, wherein the means for controlling is configured such that the first intensity level is determined based on previous sleep sessions of the subject.

20. The system of claim 15, wherein the means for causing is configured such that the first amount and the second amount are different.

21. The system of claim 20, wherein the means for causing is configured such that first amount and the second amount are determined during the first individual period of slow wave sleep.

* * * * *